United States Patent [19]

Liu et al.

[11] Patent Number: 5,028,614
[45] Date of Patent: Jul. 2, 1991

[54] HYDROXYMETHYL-INDOLIZIDINES AND QUINOLIZIDINES AND THEIR USE AS α-GLUCOSIDASE I INHIBITORS

[75] Inventors: Paul S. Liu; Mohinder S. Kang; Roland S. Rogers; Barry L. Rhinehart, all of Cincinnati, Ohio

[73] Assignee: Merrell Dow Pharmaceuticals Inc., Cincinnati, Ohio

[21] Appl. No.: 502,602

[22] Filed: Mar. 30, 1990

[51] Int. Cl.$^5$ .................. A61K 31/435; A61K 31/41; C07D 455/02
[52] U.S. Cl. .................................. 514/306; 514/299; 546/138; 546/183
[58] Field of Search ................ 546/138, 183; 514/299, 514/306

[56] References Cited

U.S. PATENT DOCUMENTS 4,797,387  1/1989  King .................................. 546/183

FOREIGN PATENT DOCUMENTS 0297534  1/1989  European Pat. Off. .

OTHER PUBLICATIONS

Nash et al., *Tetrahedron*, 44, 5959 (1988).
Nash et al., *Tetrahedron Letters*, 29(20), 2487 (1988).
Harris et al., *Tetrahedron Letters*, 30(42), 5685 (1989).
Nash et al., *Phytochemistry*, 29(1), 111 (1990).
Derwent Abstract 90-107660/14 (Issued May 16, 1990).
NTIS Report PB89-235071, Dec. 19, 1989 (U.S. Patent Application Serial No. 7/289,907, filed Dec. 23, 1988).

*Primary Examiner*—Johann Richter
*Attorney, Agent, or Firm*—John J. Kolano

[57] ABSTRACT

The present invention describes a group of polyhydroxylated indolizidines and quinolizidines and their esters. These compounds are prepared starting from 2,6-dideoxy-2,6-dideoxy-2,6-imino-1,3,4,5-tetrakis-O-(phenylmethyl)-D-glycero-L-gulo-heptitol or a corresponding N-substituted compound. The compounds are useful in the treatment of diabetes and as α-glucosidase I inhibitors.

10 Claims, No Drawings

HYDROXYMETHYL-INDOLIZIDINES AND QUINOLIZIDINES AND THEIR USE AS α-GLUCOSIDASE I INHIBITORS

BACKGROUND OF THE INVENTION

A number of hydroxylated derivatives of indolizidine and pyrrolizidine have been reported in the literature. For the most part, these compounds have been isolated from natural sources and the best known compound of this type is castanospermine which can also be named as [1S($\alpha$,6$\beta$,7$\alpha$,8$\beta$, 8a$\beta$)]-octahydro-1,6,7,8-indolizinetetrol. Pyrrolizidines having a carbon substituent (i.e., a hydroxymethyl substituent) have been reported previously [see Nash et al., Tet. Letters, 29(20), 2487 (1988); Nash et al., Tetrahedron, 44, 5959(1988)]but similarly substituted indolizidine and quinolizidines do not appear to have been described previously.

DESCRIPTION OF THE INVENTION

The present invention is directed to hydroxylated indolizidines and quinolizidines having a hydroxymethyl substituent and to esters of such compounds. More particularly, the present invention is directed to compounds having the following general formulas:

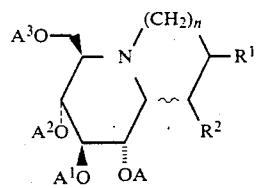

wherein n is 1 or 2; $R^1$ and $R^2$ are independently H or $OA^4$; A, $A^1$, $A^2$, $A^3$ and $A^4$ are each independently hydrogen, Cl-18 alkanoyl or

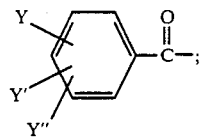

and Y, Y', and Y" are each independently hydrogen, $C_{1-4}$ alkyl, $C_{1-4}$ alkoxy rr halogen; or the pharmaceutically acceptable salts of the aforesaid compounds.

In the above structural formula, the wavy line indicates that the second ring can be fused to the six-membered (piperidine) ring shown in either of the two isomeric forms possible. In addition, where the groups $R^1$ and $R^2$ represent $OA^4$, it should be recognized that there is a secon attached at the same ring carbon and that second atom is hydrogen. Furthermore, the groups $R^1$ and $R^2$ can have either of the two possible configurations with respect to the ring structure.

The $C_{1-18}$ alkanoyl grOupS referred to above can be straight- or branched-chain and can be exemplified by formyl, acetyl, propionyl, butyryl, isobutyryl, hexanoyl, octanoyl, decanoyl and hexadecanoyl. The halogens referred to above can be exemplified by fluorine, chlorine, bromine or iodine. The $C_{1-4}$ alkyl groups referred to above, whether alone or part of an alkoxy group, can be straight- or branched-chain alkyl groups containing up to 4 carbon atoms. Examples of various such groups are methyl, ethyl, propyl, butyl, methoxy, ethoxy or butoxy.

Acid addition salts with pharmaceutically acceptable acids referred to above are equivalent to the amines for the purposes of this invention. Illustrative of such salts are the salts with inor9anic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-amino-benzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid. Such salts can be obtained by standard procedures from an amine of this invention and the appropriate acid.

In the preparation of the indolizidine compounds of the present invention wherein $R^1$ and $R^2$ are both hydrogen or —OH, 2,6-dideoxy-2,6-[[(phenylmethoxy)carbonyl]imino]-1,3,4,5-tetrakis -O-(phenylmethyl)-D-glycero-L-gulo-heptitol serves as the basic starting material. The specific series of reactions used to convert this compound to a hydroxylated indolizidine is shown in Scheme A below. In the structural formulas, Bn is phenylmethyl and Z is benzyloxycarbonyl or t-butyloxycarbonyl.

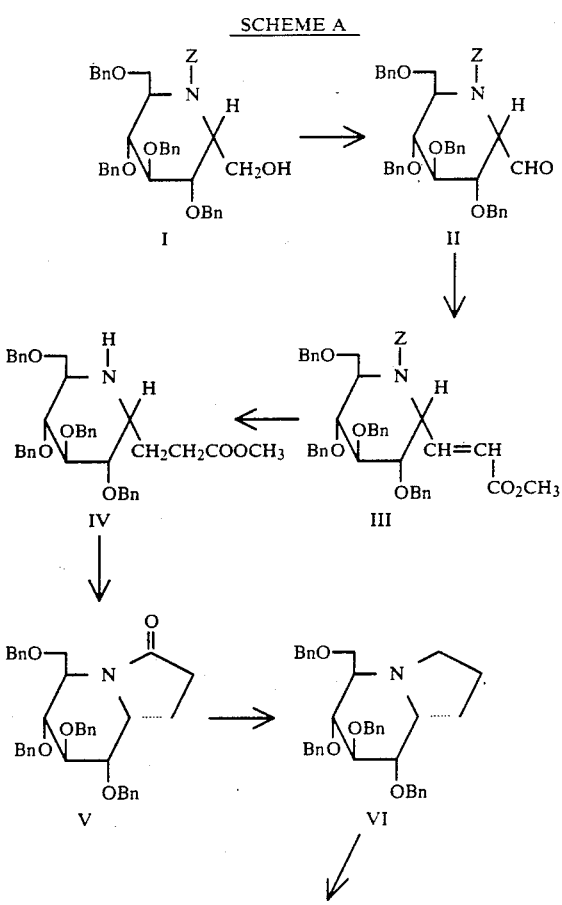

SCHEME A

-continued
SCHEME A

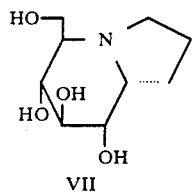

VII

Thus, the free hydroxymethyl group in the starting compound is oxidized to the corresponding aldehyde (II). Oxalyl chloride and dimethylsulfoxide in methylene chloride (Swern oxidation) can be used for this reaction. Base catalysed epimerization with 1,8-diazabicyclo[5.4.0]undec-7-ene or 1,4-diazabicyclo[2.2.2]octane gave a mixture of aldehydes epimeric at $C_2$. The aldehyde is then reacted with methyl (triphenylphosphoranylidene)acetate in a Wittig condensation to extend the carboxaldehyde group to a three-carbon, acrylate ester side chain and give compound (III). Catalytic reduction of the acrylate using hydrogen and Raney nickel gives the corresponding propionate ester (IV). Hydrolysis of the ester using formic acid gives the corresponding carboxylic acid which cyclizes spontaneously to give the corresponding lactam (V). The lactam is then reduced to the corresponding cyclic amine (VI) using a hydride reducing agent such as aluminum hydride in an inert solvent such as tetrahydrofuran. The protecting benzyl groups are then removed from VI by standard hydrogenation to give the desired polyol product (VII).

The same general procedure can be used to obtain the corresponding quinolizidine except that the appropriate reactants are used in the Wittig Condensation. That is, the aldehyde II is reacted with methyl 3-(triphenylphosphoranylidene)propionate to give a compound which corresponds to III except that the ester side chain contains four carbon atoms and is a 3-butenoate rather than an acrylate. The butenoate is then subjected to the same series of reactions as described above to give the quinolizidine which corresponds to indolizidine VII.

To obtain the compounds in which $R^1$ and $R^2$ are both —OH, the unsaturated ester III or the corresponding butenoate is cis-hydroxylated at the double bond using potassium permanganate or osmium tetroxide to give, after selective hydrogenation to remove the N-phenylmethoxycarbonyl group, the $\alpha,\beta$-dihydroxy ester corresponding to IV (or the corresponding $\beta,\gamma$-dihydroxybutanoate). The ester is then reacted as described above to give the hexahydroxy compound corresponding to VII or the corresponding quinolizidine.

The quinolizidines of the present invention in which $R^1$ is H and $R^2$ is $OA^4$ can be obtained from the cyclic carbamate VIII shown in Scheme B below. This Scheme specifically shows the conversion of VIII to a monoester XVII.

SCHEME B

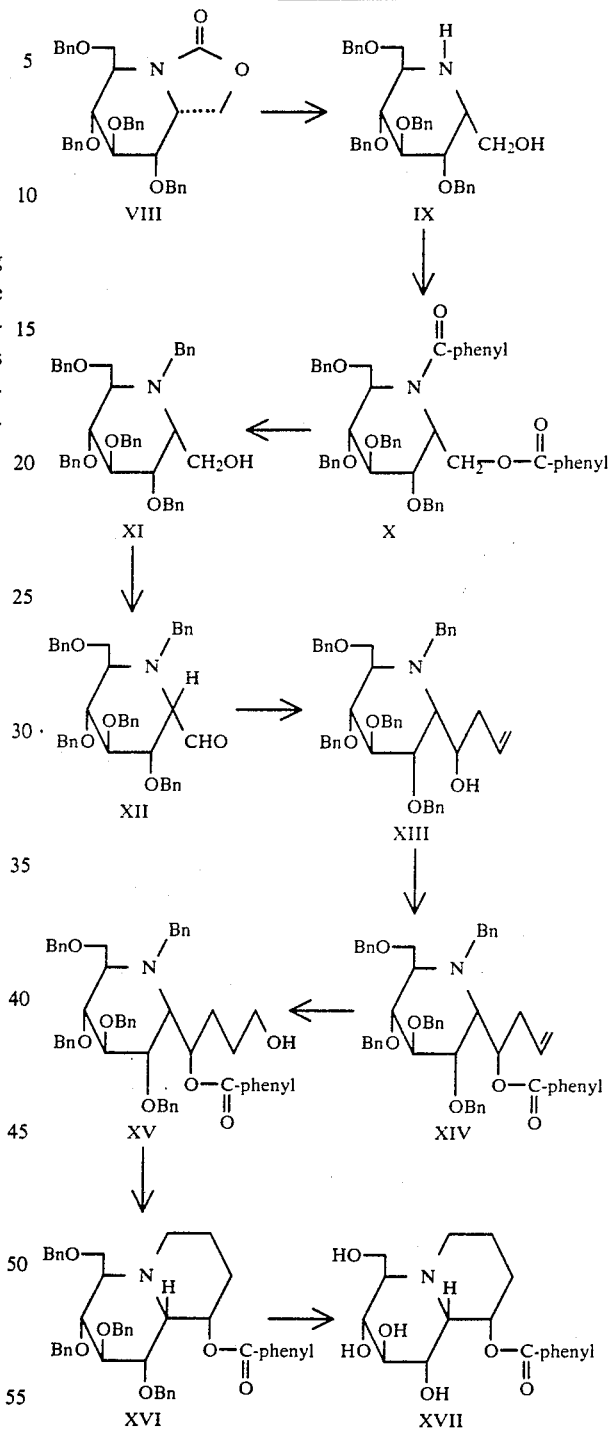

Specifically, the cyclic carbamate VIII is treated with aqueous base, such as 50% sodium hydroxide, to open the carbamate and give the hydroxymethyl compuond IX. This alcohol is then reacted with benzoyl chloride to give the N-benzoyl benzoate ester (X). Reduction of the N-benzoyl compound with a hydride reducing agent, such as aluminum hydride, gives the corresponding N-benzyl compound which, after alkaline hydrolysis, gives the N-benzyl hydroxymethyl compound (XI). Swern oxidation of this hydroxymethyl compound gives carboxaldehyde XII. The carboxaldehyde XII can also be epimerized by treatment with hindered bases such as 1,8-diazabicyclo[5.4.0]undec-7-ene or 1,4-diazabicyclo [2.2.2]octane. Reaction of the aldehyde with allylmagnesium chloride gives the carbinol XIII. This reaction gives a mixture of the epimeric carbinols which is carried through the reactions as indicated until the isomers can be separated conveniently. This carbinol is then reacted with an acid chloride to give the corresponding ester. Specifically, the benzoate is shown as compound XIV in Scheme B. Treatment of the unsaturated benzoate with borane followed by hydrogen peroxide gives the corresponding primary alcohol (XV). This procedure also gives some of the 1,4-diol (compound XVIII in Scheme C). The hydroxy ester (XV) is then reacted with cyclohexene in methanol and Pearlman's catalyst to remove the N-benzyl group. The resulting compound is then reacted with methanesulfonyl chloride to bring about cyclization and give the quinolizidine ester XVI. Catalytic hydrogenation using palladium black removes the benzyl protecting groups to give the tetrahydroxy ester XVII.

In a similar fashion, reaction of the carboxaldehyde XII instead with vinyl magnesium chloride gives the allylic alcohol with one less carbon in the side chain than carbinol XIII. The allylic alcohol is then subjected to the same series of reactions as described above to give indolizidine compounds corresponding to quinolizidine compounds XVII (above) and XXI (below). Preparation of the pentahydroxy compound corresponding to XVII is shown in Scheme C below.

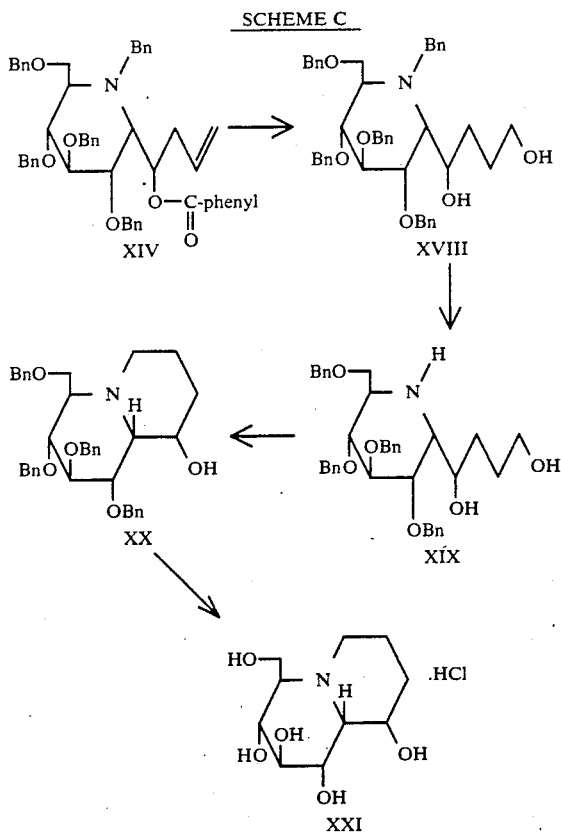

SCHEME C

Specifically, the 1,4-diol (XVIII), obtained as described earlier, is reacted with cyclohexene in methanol and Pearlman's catalyst to remove the N-benzyl protecting group and give piperidine (XIX). Reaction of the piperidine with methanesulfonyl chloride brings about cyclization to give quinolizidinol (XX). Catalytic hydrogenation of this compound using palladium black removes the benzyl protecting groups to give the desired pentahydroxy compound (XXI).

To obtain the esters of the present invention, besides those whose preparation has been described above, a polyhydroxy compound of the present invention is reacted with an appropriate acid chloride or anhydride. The resulting mixture of esters can be separated chromatographically to give individual monoesters and diesters.

Alternatively, it is possible to use a polyhydroxy compound of the present invention and protect two of the hydroxy groups as ketals and react the resulting protected compound with an appropriate acid chloride or anhydride to esterify a free hydroxy group. The protecting group is then removed to selectively give an ester. Specifically, 5R(5α,6β,7 α,8β,8aα)]octahydro-6,7,8-trihydroxy-5-hydroxymethylindolizine or 6R-(6α,7β,8α,9β,9aα]nonahydro-7,8,9-trihydroxy -6-hydroxymethylquinolizine is reacted with 2methoxypropene or 2,2-dimethoxypropane to give a cyclic ketal between the hydroxy of the more reactive hydroxymethyl group and the hydroxy on the adjacent ring carbon atom. Reaction of this cyclic ketal with an acid chloride such as butyryl chloride or benzoyl chloride preferentially gives the 8-esterified indolizidine or 9-esterified quinolizidine. The ketal protecting group is then removed by treatment with an acid such as HCl in ethanol or 4-toluenesulfonic acid to give the desired monoester.

Alternatively, the initial cyclic ketal obtained above can be reacted with carbobenzoxy chloride to give the same (8- or 9)-benzyloxycarbonate monoesters as described above. These esters can then be further reacted with an acid chloride such as butyryl chloride or benzoyl chloride to give the 7-esterified indolizidine or 8-esterified quinolizidine. The resulting product is then hydrogenated catalytically to removed the benzyloxycarbonate protecting group and then the ketal protecting group is then removed by treatment with an acid such as 4-toluenesulfonic acid to give the monoester (i.e., the indolizidine 7-monoester or quinolizidine 8-monoester).

The present compounds are useful in the treatment of diabetes. More specifically, they can be used to prevent the development of hyperglycemia which may be observed in certain diabetic conditions when a glucose precursor is ingested. Thus, when carbohydrate is ingested either as glucose or in a form such as maltose, sucrose or starch in food or drink, the serum glucose level rises to elevated concentrations. In healthy subjects, this hyperglycemic state quickly returns to normal, the glucose in the blood being rapidly metabolized and stored and/or utilized by the organism. In diabetes mellitus, however, the glucose tolerance of the patient is lowered and the abnormally high serum glucose levels which develop remain elevated for prolonged periods of time. A similar response to that seen in man can also be observed in other animals, including livestock, poultry, pet animals and laboratory animals. Such a condition can be described as postprandial hyperglycemia. One method for treating such a condition would be by administration of some agents which would prevent the conversion of complex sugars to glucose and thus prevent the development of the excessive glucose levels. In the present invention, it has been found that, where the high levels of glucose are a result of the hydrolysis of complex sugars, administration of the present compounds inhibits the initial formation of glucose in the blood and thus makes it possible to avoid the problems which would be associated with prolonged high levels of serum glucose.

The mechanism whereby this result is achieved is the following although the utility described above should not be limited by the precise details of this mechanism. Enzymes which catalyze the hydrolysis of complex carbohydrates convert non-absorbable carbohydrate into absorbable sugars. The rapid action of these enzymes lead to acute and undesirable elevations in blood glucose in diabetes. The compounds of the present invention are potent inhibitors of these enzymes and, when co-administered with a carbohydrate meal, they prevent harmful hyperglycemic excursions of this type. It is desirable, however, that the inhibition of these hydrolytic enzymes be limited to those present in the intestines and that is true for the present compounds. Otherwise, inhibition of systemic glycohydrolases or glucose transport can lead to difficulty in the utilization of intracellular carbohydrates as an energy source and thus cause metabolic problems.

The following test procedure can be used to demonstrate the activity of the present compounds.

In vitro studies. Intestinal glucohydrolases were isolated from rat intestine. Male 150- to 250-g rats were fasted overnight and sacrificed by $CO_2$ anesthesia. The entire small intestine was removed, flushed with 50 to 100 ml of cold saline and placed on an ice-cold glass plate. The mucosal layer was removed and homogenized in 5 times its volume of 0.5 M NaCl, 0.5 M KCl and 5 mM EDTA, pH 7.0. This homogenate was centrifuged at 20,000× g for 30 min and the pellet washed by suspension and recentrifugation three times in fresh salt solution. The resulting pellet was finally homogenized in 5 times its volume of 0.9% NaCl and centrifuged at 200× g for 10 min. The incubation mixtures contained 10 μl of this enzyme preparation plus 3.3 μmole of sucrose and test compound in a final volume of 100 μl of 0.1 M sodium maleate buffer, pH 5.9. All determinations were performed in duplicate or triplicate. One set of determinations was heat inactivated at 90° C. for 2 min immediately after adding the enzyme. The others were incubated for 30 min at 37° C. in a water bath and then heat inactivated. Glucose concentrations were determined by glucose dehydrogenase (Seragen Diagnostics, Indianapolis, Ind.). Glucose produced at each concentration of test compound was compared with that produced with no drug present.

When [5R-(5α,6β,7α,8β,8aα)]-octahydro-6,7,8-trihydroxy-5-hydroxymethylindolizine was tested according to this procedure, it showed an $IC_{50}$ of about 2μM against sucrase.

In practicing a method of this invention, an amount of one of the compounds effective to inhibit postprandial hyperglycemia is administered to a mammal in need thereof by a suitable route. For the purposes of this invention, oral administration is preferred.

The effective amount of the compound, that is, the amount sufficient to inhibit postprandial hyperglycemia, depends on various factors such as the size, type and age of the animal to be treated, the particular compound or pharmaceutically acceptable salt employed, the frequency of administration, the severity of the condition and the time of administration. Generally speaking, the compounds would be administered orally at a dose of 0.5 mpk to 50 mpk, with a dose of 1.5 mpk to 15 mpk being preferred. More specifically, the present compounds would be administered to humans in single unit doses containing 100 mg to 1 g of active ingredient with the material being administered three time a day at mealtime.

The compounds of the present invention are also useful as anti-viral agents and, more particularly, they are useful against retroviruses such as HIV. This utility is established by the fact that the present compounds are inhibitors of α-glucosidase I and thus block the first reaction step in glycoprotein processing of the viral envelope glycoproteins. Without this first biosynthetic step, the virus can not function properly and it would be inhibited. Thus, it has been established that inhibitors of α-glucosidase I would also be useful as antiviral agents and particularly as inhibitors of retroviruses such as HIV. [Sunkara et al. Biochem. Biophys. Res. Commun., 148 (1), 206-210 (1987); Tyms et al. Lancet, ii, 1025-1026 (1987).]The activity of the present compounds as inhibitors of α-glucosidase I can be demonstrated by the following test procedure.

Preparation of [$^3$H] Glucose Labeled Substrate:

The [$^3$H] glucose labeled oligosaccharides substrate ($G_3M_9N$) for glucosidase I was prepared by metabolically labeling exponentially growing BHK cells with [$^3$H]galactose in the presence of 200μg/ml of castanospermine. BHK cells grown as monolayer were treated with 200μg/ml of castanospermine in DMEM (#430-1600) supplemented with 10% heat inactivated fetal calf serum, 2 mM L-glutamine and 1X of PSN antibiotic mixture. After three hour incubation with castanospermine, [1-$^3$H] galactose (10μci/ml of media) was added to label the glycoproteins and cells were allowed to grow to confluency for an additional 48 hours. At the end of labeling period, the cells were washed with cold PBS and scraped with a rubber policeman. Cell pellet was heated for 10 minutes at 100° C. and exhaustively treated with pronase (usually 72 hrs) in 50 mM Tris pH 7.5 containing 10 mM CaCl2 and 1% Pronase under toluene atmosphere to obtain glycopeptides. The glycopeptides were separated on columns of Bio-gel P-4. The glycopeptides peak produced by castanospermine treatment was pooled, treated with Endo-H to release the oligosaccharides. The oligosaccharides obtained by endo-H hydrolysis were bound to a ConA column previously washed with buffer A (50 mM Tris pH 7.5 containing 500 mM NaCl) and equilibrated with buffer B (5 mM Sodium acetate buffer pH 5.5 containing 2 mM of each $CaCl_2$, $MgCl_2$ and $MnCl_2$). The oligosaccharides were then eluted with buffer B containing 100 mM α-methylmannoside. The oligosaccharides eluted from ConA column were further purified and characterized on a calibrated Biogel P-4 column (1.5×200 cm, (−) 400 mesh). The purified oligosaccharides having $GLc_3Man_9GlcNAc$ structure were used as substrate in these studies.

Preparation of Test Compounds

Compounds were dissolved in $H_2O$ or DMSO as appropriate and usually 0.02 to 100 μg/ml concentration of the compound was added to the enzyme before starting the reaction with the radioactive substrate. DMSO controls were run for each experiment, if DMSO was used to dissolve the compounds.

Microtiter Plate Assay for α-Glucosidase I Activity

ConA-sepharose was washed first with buffer A, then with buffer B as described above, and resuspended in buffer B (gel: buffer, 1:1) before use. The enzymatic assays were performed in a 96 well microplate in a total volume of 100 μl which contained 5000 CPM of [$^3$H]G$_3$M$_9$N substrate, 100 mM potassium phosphate buffer pH 6.8 and purified α-glucosidase I. The reaction mixture was incubated at 37° C. for one hour for each experiment and the reaction stopped by adding 25 μl of glacial acetic acid. To the mixture, 175 μl of concanavalin A-sepharose in buffer B (1:1) was added and microplate was spun at 500× g for 5 minutes. A 150 μl aliquot of supernatant was removed and counted. When Compound VII in Scheme A above was tested by this procedure, it showed an IC$_{50}$ of 0.3 μM. When compound XVII in Scheme B above was tested by this procedure, it showed an IC$_{50}$ of 29μM. Compound XXI in Scheme C above showed an IC$_{50}$ of 0.15μM in this test.

Inhibition of Glucosidase I in F-10 Cells:

Accumulation of G$_3$ (G$_3$MsN$_2$ -Asn) in F-10 cells is used as a measure of inhibition of α-9lucosidase I. The qlycopeptides obtained (as above for BHK cells) by pronase digestion of radio labeled F-10 cells in the presence of different concentration of inhibitors (usually 0.1 to 30 μg/ml) are chromatographed on Bio-gel PD-6. The relative percentage of counts in G$_3$ peak as compared to void volume (where the radioactivity in the controls is eluted) are used as a measure of inhibitory activity of a particular compound.

The compounds of this invention can be used to treat a number of diseases and conditions known to be caused by pathogenic viruses including those diseases and conditions caused by murine leukemia virus, feline leukemia virus, cytomegalo-virus (CMV), avian sarcoma virus, human immunodeficiency virus (HIV), HTLV-I, and HTLV-II. Those experienced in this field are readily aware of the circumstances requiring anti-retroviral therapy. Applicants consider the use of the compounds of this invention to treat HIV infections in humans to be of most importance. The term "patient" used herein is taken to mean mammals such as primates, including humans, sheep, horses, cattle, pigs, dogs, cats, rats and mice.

The amount of a compound of the present invention to be administered can vary widely according to the particular dosage unit employed, the period of treatment, the age and sex of the patient treated, the nature and extent of the disorder treated, and the particular parent compounds or ester derivative selected. Moreover the derivative can be used in conjunction with other agents (e.g. AZT) known to be useful in the treatment of retroviral diseases and agents known to be useful to treat the symptoms of and complications associated with diseases and conditions caused by retroviruses. The anti-retrovirally effective amount of a compound of the present invention to be administered will generally range from about 15 mg/kg to 500 mg/kg. A unit dosage may contain from 25 to 500 mg of the parent compound or ester derivative, and can be taken one or more times per day. The compound used can be administered with a pharmaceutical carrier using conventional dosage unit forms either orally or parenterally.

In practicing the methods of this invention, the active ingredient is preferably incorporated in a composition comprising a pharmaceutical carrier and from about 5 to about 90 percent by weight of a compound of the invention or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, elixirs, syrups, emulsions, dispersions and wettable and effervescent powders, and can contain suitable excipients know to be useful in the preparation of the particular type of composition desired. Suitable pharmaceutical carriers and formulation techniques are found in standard texts, such as *Remington's Pharmaceutical Sciences*, Mack Publishing Company, Easton, Penna.

The following examples are presented to illustrate the present invention. However, they should not be construed as limiting it in any way.

EXAMPLE 1

To a solution of oxalyl chloride (2.0 mL, 22 mmol) in methylene chloride (16 mL), cooled at −78° C., was added dropwise a solution of dimethyl sulfoxide (3.0 mL, 40 mmol) in methylene chloride (8 mL) and the resulting mixture was stirred for 15 mins. 2,6-Dideoxy-2,6-[[(phenylmethoxy)-carbonyl]imino]-1,3,4,5-tetrakis-O-[phenylmethyl]-D-qlYcero-L-qulo-heptitol (8.29, 11.94 mmol), dissolved in 20 mL of methylene chloride, was added dropwise to the above mixture and stirred for an additional 15 min. Triethylamine [8 mL] was then added and the mixture was allowed to warm to 0° C. The mixture was washed with 1N hydrochloric acid (50 mL), saturated sodium bicarbonate solution (2×50 mL) and brine (50 mL). After drying over magnesium sulfate, the organic phase was evaporated in vacuo to provide the aldehyde as light yellow oil (7.7 g, 94%); IR (neat) 1700 cm$^{-1}$ (C=O). $^1$H NMR (CDCl$_3$) δ 3.2–4.7 (m, 15H), 5.00 (s, 2, COOCH$_2$Ph), 7.2 (m, 25, aryl), 9.60 (s, 1, —CHO). The crude aldehyde (II) obtained was used without further purification in the next step in a Wittig condensation.

To a solution of the above aldehyde (II) (3.7 9, 5.4 mmol) in 30 mL of dimethoxyethane was added methyl (triphenylphosphoranylidene)acetate (2.7 9, 8.1 mmol) and the mixture was stirred under nitrogen at ambient temperatures for 3 days. The reaction mixture was diluted with ethyl acetate (50 mL) and filtered. The filtrate was washed with 0.1N hydrochloric acid solution (50 mL), saturated sodium bicarbonate solution (2×50 mL) and brine (50 mL). After drying over magnesium sulfate, the organic phase was evaporated to a syrupy residue and purified by flash chromatography (silica gel, 1:3 ethyl acetate:hexane) to provide the α,β-unsaturated ester (III) as a colorless oil (3.51 g, 87%); IR (neat) 1712 cm$^{-1}$ (C=O). $^1$H NMR (CDCl$_3$) δ 3.3–4.9 (m, 18H), 5.1 (s, 2H, —COOCH$_2$Ph), 5.90 (d, 1H, J=16 Hz, =CH—CO$_2$CH$_3$), 7.00 (dd, 1H, —CH=CH=CO$_2$CH$_3$), 7.2 (m, 25H, aryl). MS (CI-CH$_4$) 742 (MH+).

EXAMPLE 2

To a solution of Compound (III) (1.85 g, 2.5 mmol) in methylene chloride (3 mL) was added 30 mL of ethanol containing 1 g of Raney Nickel. The mixture was hydrogenated on a Parr apparatus for 5 hours at a pressure of 1.7 atmospheres of hydrogen. The reaction mixture was filtered through celite and the filtrate was evaporated to dryness to an oily residue which was redissolved in ethyl acetate (30 mL) and washed with aqueous saturated sodium bicarbonate solution (2×40 mL) and brine (40 mL). The organic phase was dried over magnesium sulfate and evaporated to provide an oil which was dissolved in ethanol (20 mL) containing 10 drops of 97% formic acid. The alcoholic solution was heated under reflux for 6 hours and then diluted with toluene (40 mL). The mixture was concentrated to provide a syrupy residue. The residue was dissolved in ethyl acetate (40 mL) and the organic solution was washed with aqueous saturated sodium bicarbonate solution (50 mL) and brine (50 mL), and finally dried over magnesium sulfate. Evaporation of solvents from the organic phase gave lactam (V) as an oil (1.40 g, 97%); IR (neat) 1686 cm$^{-1}$ (CO—N<). $^1$H NMR (CDCl$_3$) δ 1.9–2.6 (m, 4H), 3.4–4.0 (m, 6H), 4.3–4.7 (m, 9H), 7.1 –7.4 (m, 20H, aryl). MS (CI—CH$_4$) 578 (MH$^+$), 456 (MH$^+$—PhCH$_2$-O-CH$_3$).

EXAMPLE 3

A solution of Compound (V) (1.4 g, 2.4 mmol) in tetrahydrofuran (20 mL) was added dropwise to a stirred slurry of aluminum hydride (7 mmol) in tetrahydrofuran (30 mL) at 0° C. After addition, the mixture was stirred at room temperature for an hour. Distilled water (5 mL) and 2N sodium hydroxide solution (20 mL) were added successively to the reaction mixture. After mixing, the phases were separated and the aqueous layer was extracted twice with ethyl acetate (50 mL). The organic phase was washed with aqueous saturated sodium bicarbonate (100 mL) and brine (100 mL), and finally dried over magnesium sulfate. Evaporation of solvents from the organic extracts gave Compound (VI) as an oily residue (1.30 g, 95%); IR (neat) no absorbance at 1650–1700 cm$^{-1}$. $^1$H NMR (CDC13) δ 1.6–2.2 (m, 4H), 3.1–4.2 (m, 9H), 4.4–4.8 (m, 8H), 7.2–7.4 (m, 20H, aryl). MS (CI—CH$_4$) 564 (MH$^+$), 456 (MH$^+$—PhCH$_2$OH), 442 (MH$^+$—PhCH$_2$OCH$_3$).

EXAMPLE 4

[5R-(5α,6β,7α,8β,8aα)]octahvdro-6,7,8-trihvdroxv-5-hydroxymethylindolizine

To a solution of Compound VI (1.30 g, 2.3 mmol) in glacial acetic acid (10 mL) was added 10% Pd/C (250 mg) and the mixture was hydrogenated on a Parr apparatus at 2.7 atmospheres and 50° C. for 18 hours. The mixture was filtered through celite and diluted with 30 mL of xylene. Evaporation of solvents from the filtrate gave a glassy residue which was redissolved in methanol (5 mL) and ether was added until the solution was slightly cloudy. Upon refrigeration at 4° C., 5R-(5α,6β,-7α,8β,8aα)]octahydro-6,7,8-trihydroxy-5-hydroxymethylindolizine (VII) precipitated from the mixture as a white solid and was collected (0.35 g, 75%) mp. 218–222° C. (with decomposition). IR 3600–3200 cm$^{-1}$ (OH). $^1$H NMR (D$_2$O) δ 1.6–2.0 (m, 4H), 2.35-2.85 (m, 2H), 3.2-3.35 (m, 2H), 3.40 (t, 1H), 3.60 (t, 1H), 3.8–3.9 (m, 3H). MS (CI—CH$_4$) 204 (MH$^+$), 186 (MH$^+$—H$_2$O), 172 (MH$^+$—CH$_3$OH). This compound has the following structural formula:

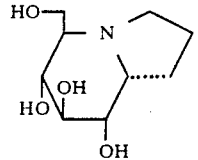

EXAMPLE 5

If the procedure described in the second paragraph of Example 1 is repeated using methyl 3-(triphenylphosphoranylidene)propionate in place of the methyl (triphenylphosphoranylidene)acetate, the corresponding β,γ-butenoate ester is obtained. This product is then further reacted according to the procedures described in Examples 2, 3 and 4 to give the 7,8,9-trihydroxy-6-hYdroxymethyl quinolizidine which has the following formula:

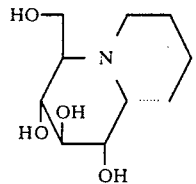

EXAMPLE 6

To a suspension of 2,6-(carboxyimino)-2,6-dideoxy-3,4, 5,7-tetrakis-O-(phenylmethyl)-D-glycero-D-idoheptitol, instramol. 2,1-ester (VIII) (9.00 g; 15.5 mmoles) in ethanol (40 mL), 50% NaOH (6.3 mL) and water (6 mL) were added. The suspension was then heated under reflux for 16 hours. After cooling to room temperature, the solvent was removed under reduced pressure. Water (10 mL) was added to the residue, and the mixture was extracted with ether (2×70 mL). The combined organic solution was dried over magnesium sulfate and the solvent evaporated under reduced pressure. Upon storing under vacuum, 2,6-dideoxy-2,6-imino-1,3,4,5-tetrakis -O-(phenylmethyl)-D-qlvcero-L-oulo-heptitol (IX) (8.2 g; 96.1%) crystallized as a white solid. MP 76°–78° C.; MS (CI—CH$_4$) 554 (MH$^+$), 446 (MH$^+$—PhCH$_2$OH); IR (KBr) no aborbance 1720–1770 cm$^{-1}$; $^1$H nmr (CDC13) δ 2.8 (dt, 1H), 3.3–3.4 (m, 1H), 3.4–3.6 (m, 2H), 3.6–3.8 (m, 4H), 3.8–3.9 (dd, 1H), 4.4–4.5 (m, 3H), 4.7 (s, 2H), 4.8–4.9 (m, 3H), 7.2–7.4 (m, 20H).

EXAMPLE 7

To a solution of alcohol (IX) (5.80 g; 10.5 mmoles) and triethylamine (7.3 mL; 52.4 mmoles) in methylene chloride (25 mL) at 0° C., benzoyl chloride (3.9 mL; 33.5 mmoles) was added dropwise under an atmosphere of dry nitrogen. The reaction mixture was warmed to room temperature and stirred for 16 hours. Distilled water (5 mL) and saturated aqueous sodium bicarbonate solution (50 mL) were added and mixed thoroughly. The layers were separated, and the aqueous phase was extracted with methylene chloride (50 mL). The combined organic solution was dried over sodium sulfate and the solvent was evaporated. The resulting crude residue was purified via flash chromatography (silica gel; 1:4 ethyl acetate:hexane) to yield [2R-(2α,3,4β,5α,6β)]-1-benzoyl-3,4,5-tris (phenylmethoxy)-6-

[(phenylmethoxy)methyl]-2-piperidinemethanol benzoate (ester) (X) (7.57 g; 94.8%) as a light yellow oil. MS (FAB in MNBA), 762.3 (MH+), 654.2 (MH+—PhCH20H); IR (neat) 1720 cm$^{-1}$ (O=C—O), 1647 (O=C—N); 1H nmr (CDCl$_3$) δ 3.7-4.9 (m, 17H), 7.1-7.4 (m, 27H), 7.5 (t, 1H), 7.95 (d, 2H).

EXAMPLE 8

A solution of Compound (X) (7.50 g; 9.84 mmoles) in tetrahydrofuran (10 mL) was added dropwise to a suspension of AlH3 (41.3 mmoles) in tetrahydrofuran (50 mL) at 0° C. The reaction was heated under reflux for 18 hours. Upon cooling to 0° C., a mixture of water and tetrahydrofuran (10 mL; 2:1) was added, followed by a 50% NaOH solution (80mL). The resultant mixture was extracted with ether (3×50 mL), and the combined organic solution was dried over magnesium sulfate, filtered, and evaporated to an oil. The oil was purified via flash chromatography (silica gel; 1:4 ethyl acetate:hexane) to yield [2R-(2α,3α,4β,5α,6β)]-3,4,5-tris (phenylmethoxy)-6-[(phenylmethoxy)methyl]-1-(phenylmethyl)-2-piperidinemethanol (XI) (5.91 g; 91.8%) as a clear, colorless oil. IR (neat) no absorbance 1650-1720 cm$^{-1}$; MS (CI—CH$_4$) 644 (MH+), 536 (MH+—PhCH$_2$OH); $^1$H nmr (CDCl$_3$) δ 3.1 (m, 2H), 3.5-4.0 (m, 7H), 4.2 (d, 1H), 4.4 (d, 2H), 4.6 (m, 2H), 4.7 (s, 2H), 4.9 (m, 3H), 7.1-7.5 (m, 25H).

EXAMPLE 9

To a solution of oxalyl chloride (1.9 mL; 21.4 mmoles) in methylene chloride (30 mL), cooled at −78° C. was added dropwise a solution of dimethyl sulfoxide (3.1 mL; 42.9 mmoles) in methylene chloride (6 mL). The resulting mixture was stirred for 5 minutes, then a solution of Compound (XI) (4.6 g; 7.14 mmoles) in methylene chloride (15 mL) was added over 15 minutes. After stirring the mixture for 10 additional minutes, a solution of triethylamine (10.9 mL; 78.6 mmoles) in methylene chloride (5 mL) was added, and the reaction was warmed to room temperature. Water (15 mL) was added and the layers were separated. The aqueous solution was extracted with methylene chloride (30 mL), and the combined organic solution was dried over sodium sulfate and the solvent evaporated under reduced pressure. The resulting oil was purified via flash chromatography (silica gel; 1:4 ethyl acetate:hexane) to yield [2S(2α,3α,4β,6α,6β) ]-3,4,5-tris(phenylmethoxy)-6-[(phenylmethoxy)methyl]-1-(phenylmethyl)-2-piperidinecarboxaldehyde (XII) (4.44 g; 96.9%) as a light yellow oil. IR (neat) 1702 cm$^{-1}$ (C=O); MS (CI—CH$_4$) 642 (MH+), 612 (MH+—H$_2$CO); $^1$H nmr (CDCl$_3$) δ 3.2-4.2 (m, 7H), 4.4 (s, 2H), 4.5-5.0 (m, 8H), 7.1-7.4 (m, 25H), 9.9 (s, 1H).

EXAMPLE 10

To a solution of aldehyde (XII) (4.00g; 6.23 mmoles) in diethyl ether (25 mL), cooled at −78° C., was added a 2M solution of allylmagnesium chloride (7.8 mL; 15.6 mmoles). The reaction was kept at −10° C. for 16 hours. Upon warming to 0° C., water (2 mL) and 3N hydrochloric acid solution (30mL) were added. After separating the phases, the aqueous layer was extracted with methylene chloride (2×30 mL). The combined organic solution was dried over magnesium sulfate and the solvent evaporated under reduced pressure. The resulting oil was purified via flash chromatography (silica gel; 1:4 ethyl acetate:hexane) to yield 3,4,5-tris(phenylmethoxy) -6-[(phenylmethoxy)methyl]-1-(phenyl-methyl) -α-(2-propenyl)-2-piperidinemethanol (XIII) (3.0 g; 70.4%) as a light yellow oil. In this compound, the stereochemistry of the substitution on the piperidine ring is the same as in the starting material. IR (neat) no absorbance at 1650-1710 cm$^{-1}$; MS (FAB-MNBA) 684 (MH+), 612 (MH+—C$_4$H$_7$OH); $^1$H nmr (CDCl$_3$) δ 2.0 (m, 1H), 2.6 (m,1lH), 2.8 (dd, 1H), 3.2 (m, lH) 3.5-4.0 (m, 6H), 4.3 (d, 1H), 4.4 (s, 2H), 4.5-5.0 (m, 8H), 5.6-5.8 (m, 1H), 7.1-7.4 (m, 25H).

EXAMPLE 11

To a solution of Compound (XIII) (3.00 g; 4.40 mmoles) and triethyl amine (2.4 mL; 17.6 mmoles) in methylene chloride (25 mL), cooled at 0° C., was added benzoyl chloride (1.6 mL; 13.2 mmoles). The reaction was kept at room temperature for 16 hours, then water (5 mL) and saturated aqueous sodium bicarbonate solution (40 mL) were added. The phases were separated, and the aqueous phase was extracted with methylene chloride (30 mL). The combined organic solution was dried over sodium sulfate and the solvent evaporated under reduced pressure. The crude oil was purified via flash chromatography (silica gel; 1:4 ethyl acetate:hexane) to yield 3,4,5-tris(phenylmethoxy)-6-[(phenylmethoxy) methyl]-1-(phenylmethyl)-α-(2-propenyl)-2-piperidinemethanol benzoate (ester) (XIV) (1.92 g; 56%) as a clear, colorless oil and recovered Compound (XIII) (0.60 g; 0.88 mmoles). IR (neat) 1719 cm$^{-1}$ (C=O); MS (FAB-MNBA) 788 (MH+), 680 (MH+—PhCH$_2$OH); $^1$H nmr (CDCl$_3$) δ 2.4 (m, 1H), 2.9 (dt, 1H), 3.5-4.0 (m, 8H), 4.1 (d, 1H), 4.4 (s, 2H), 4.5-4.9 (m, 9H), 5.4-5.6 (m, 1H), 7.1-7.4 (m, 27H), 7.5 (m, 1H), 8.1 (m, 2H).

EXAMPLE 12

To a solution of Compound (XIV) (1.80 g; 2.29 mmoles) in tetrahydrofuran (25 mL), cooled at 0° C., was added a 1.0M solution of borane-dimethylsulfide complex in tetrahydrofuran (1.5 mL). The reaction was warmed to room temperature and kept for 20 hours. After cooling to 0° C., 3N NaOH solution (15 mL) and 30W% hydrogen peroxide (0.5 mL) were added, and the suspension was heated under reflux for 1 hour. Upon cooling to room temperature, the suspension was mixed with water (10 mL) and extracted with ether (2×40 mL). The combined organic solution was washed with saturated sodium chloride solution, dried over magnesium sulfate and filtered. The solvent was evaporated under reduced pressure, and the crude residual oil was purified via flash chromatography (silica gel; 1:2 ethyl acetate:hexane) to yield the primary alcohol, 1-[3,4,5-tris(phenylmethoxy)-6[(phenylmethoxy) methyl]-1-(phenylmethyl)-2-piperidinyl]-1,4-butanediol 1-benzoate (XV), as a clear, colorless oil (1.05 g; 56.9%) and the 1,4-diol, 1-[3,4,5-tris (phenylmethoxy)-6-[(phenylmethoxy)methyl]-1-(phenylmethyl) -2-piperidinyl]-1,4-butanediol (XVIII), as a yellow oil (0.41 g; 24.9%). Compound (XV): IR(neat) 1720 cm$^{-1}$ (C=O); MS (FAB-MNBA) 806 (MH+), 788 (MH+H$_2$O); $^1$H nmr (CDCl$_3$) δ 1.5-1.9 (m, 2H), 2.8 (t, 1H), 3.4 (t, 2H), 3.5 (m, 1H), 3.7-4.2 (m, 7H), 4.3-4.4 (m, 1H), 4.4 (s, 2H), 4.5-4.9 (m, 7H), 5.4-5.5 (m, 1H), 7.0-7.4 (m, 27H), 7.5 (m, 1H), 8.1 (m, 2H).

EXAMPLE 13

To a solution of Compound (XV) (0.60 g; 0.74 mmoles) and cyclohexene (5 mL) in methanol (30 mL), Pearlman's catalyst (0.2 g) was added under a nitrogen atmosphere. The suspension was stirred at room temperature for 18 hours, then the catalyst was filtered through Celite and washed with methanol (20 mL). The combined organic layer was evaporated under reduced pressure to yield a crude oil, which was purified via flash chromatography (silica gel; 1:1 as a clear colorless oil (0.34 g) and recovered Compound (XV) (0.10 g; 16% recovery). The N-debenzylated alcohol (0.34 g) was dissolved in pyridine (20 mL) and cooled to $-10°$ C., then methanesulfonyl chloride (0.04 mL) was added, and reaction was continued for 96 hours. The solvent was evaporated under reduced pressure and saturated aqueous sodium bicarbonate solution was added to the residue. After extraction with ether (2×60 mL), the combined organic solution was dried over magnesium sulfate and the solvent evaporated under reduced pressure. The crude product was purified via flash chromatorgraphy (silica gel; 1:1 ethyl acetate:hexane) to yield Octahydro-7,8,9-tris (phenylmethoxy)-6-[(phenylmethoxy)methyl]-2H-quinolizin1-ol benzoate (ester) (XVI) (0.16 g; 50%) as a colorless oil. IR (film from CDCl$_3$) 1718 cm$^{-1}$ (C=O); MS(CI—CH$_4$) 698 (MH$^+$), 576 (MH$^+$—PhCO$_2$H); $^1$H nmr (CDCl$_3$) δ 1.2 (m, 1H), 1.6-1.9 (m, 2H), 2.2 (d, 1H), 2.8 (t, 1H), 3.3-3.4 (m, 2H), 3.5-3.7 (m, 3H), 3.8 (m, 1H), 4.1 (t, 1H), 4.3 (d, 1H), 4.4-4.7 (m, 7H), 4.9 (d, 1H), 5.5 (s, 1H), 7.0-7.4 (m, 22H), 7.5 (m, 1H), 8.1 (m, 2H).

EXAMPLE 14

A solution of Compound (XVI) (0.16 g; 0.24 mmoles) in glacial acetic acid (15 mL) was hydrogenated at 3.7 atmospheres in the presence of Palladium black (0.02 g) for 68 hours. The mixture was filtered through Celite and the Celite pad was washed with glacial acetic acid (10 mL). The combined acid solution was evaporated under reduced pressure. The resulting residue was redissolved in xylene and evaporated under reduced pressure to yield a reddish residue. After dissolution in methanol and treatment with Norit (0.10 g) the residue crystallized to yield [1S-(1α,2β,3α,4β,9α,9aβ) ]-octahydro-4-(hydroxymethyl)-2H-quinolizine-1,2,3,9-tetrol 9-benzoate (XVII) (0.07 g; 85%) as a white, hygroscopic solid. IR (film) 1714 cm$^{-1}$ (C=O); MS (CI—CH$_4$) 338 (MH$^+$), 216 (MH$^+$—PhCO$_2$H); $^1$H nmr (CD$_3$OD) δ 1.3 (m, 1H), 1.7-2.0 (m, 2H), 2.2 (dt, 1H), 2.8 (m, 1H), 3.3-4.0 (m, 8H), 5.5 (m, 1H), 7.8 (m, 2H), 7.9 (m, 1H), 8.2 (m, 2H).

EXAMPLE 15

To a solution of Compound (XVIII), obtained above in the synthesis of Compound (XV), (0.4 g, 0.57 mmoles), and cyclohexene (10 mL) in methanol (20 mL), Pearlman's catalyst (0.05 g) was added, and the suspension was stirred under nitrogen for 20 hours. The catalyst was filtered with the aid of Celite, and washed with methanol (50 mL). The methanolic solution was evaporated under reduced pressure, and the resulting oil was purified via flash chromatography (silica gel; 1:1 ethyl acetate:hexane) to yield 1-[3,4,5-tris (phenylmethoxy)-6-[(phenylmethoxy)methyl]-2-piperidinyl]-1,4-butanediol (XIX) (0.26 g, 75%) as a light yellow oil. IR (film from CDCl$_3$) 3412 cm$^{-1}$ (—OH); MS (CI—CH$_4$) 612 (MH$^+$), 522 (MH$^+$—PhCH$_2$.$^+$H.); $^1$H nmr (CDCl$_3$) δ 1.1-1.5 (m, 4H), 2.8-3.1 (m, 2H), 3.3-3.9 (m, 6H), 4.0—4.3 (m, 2H), 4.3-4.9 (m, 8H), 7.1-7.4 (m, 20H).

EXAMPLE 16

To a solution of Compound (XIX) (0.22 g, 0.36 mmoles) in pyridine (15 mL), cooled at $-10°$ C., methanesulfonyl chloride (0.03 mL, 0.39 mmoles) was added. After 6 days, the mixture was evaporated under reduced pressure. The resulting oil was treated with water (5 mL) and saturated aqueous sodium bicarbonate solution (20 mL), then extracted with ether (2×30 mL). The combined organic solution was dried over magnesium sulfate and the solvent evaporated under reduced pressure. Trituration of the resulting oil with ether yielded [1S-(1α,6β,7α,8β,9α,9aβ)]-octahydro-7,8,9-tris (phenylmethoxy)-6-[(phenylmethoxy)methyl]-2H-quinolizin-1-ol (XX) as white crystals (0.13 g, 60.8%) m.p. 103°-5° C.; IR (KBr) no absorbance 1650-1770 cm$^{-1}$; MS (CI13 CH$_4$) 594 (MH$^+$), 486 (MH$^+$—PhC-H$_2$OH); $^1$H nmr (CDCl$_3$) δ 1.2 (m, 1H), 1.4-1.6 (m, 3H), 1.8-2.0 (m, 2H), 2.6-2.8 (t, 1H), 3.0-3.1 (d, 1H), 3.2-3.3 (m, 1H), 3.5-3.9 (m, 4H), 4.2-5.0 (m, 9H), 7.1-7.4 (m, 20H).

EXAMPLE 17

A solution of Compound (XX) (0.12 g, 0.20 mmoles) in glacial acetic acid (10 mL) was hydrogenated at 3.3 atmospheres (H$_2$) with Palladium black (0.04 g) as the catalyst. After 72 hours, the catalyst was filtered onto a pad of Celite and washed with glacial acetic acid (10 mL). The combined acid solution was evaporated under reduced pressure to yield a reddish oil. The oil was dissolved in xylene (30 mL) and evaporated again under reduced pressure. The resultant residue was dissolved in methanol (30 mL) and treated with activated charcoal (0.08 g) for 10 minutes. The mixture was filtered, and the filter pad was washed with methanol (15 mL). The methanolic solution was condensed under reduced pressure and a solution of dry hydrogen chloride in methanol (2 mL) was added. Upon addition of ether, [1S-(1α,2β,3α,4β,9α,9aβ)]-octahydro-4-(hydroxy-methyl)-2H-quinolizine-1,2,3,9-tetrol hydrochloride (XXI) crystallized as a white solid (0.007 g, 14.9%). m.p. 152°-4° C. (with decomp.); IR (KBr) 3100 3600 cm-1 (br); MS (CI-CH$_4$) 234 (MH$^+$), 216 (MH$^+$—H$_2$O), 202 (MH$^+$—CH$_3$OH); 1H nmr (CD$_3$OD) δ 1.6-2.2 (m, 4H), 3.1 (m, 1H), 3.4 (dd, 1H), 3.5 (dd, 1H), 3.7-3.8 (m, 2H), 3.9 (m, 1H), 4.0-4.2 (m, 2H), 4.25 (t, 1H), 4.5 (m, 1H).

What is claimed is:

1. A compound of the formula:

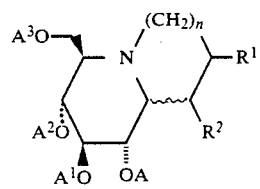

wherein n is 1 or 2; R$^1$ or R$^2$ are independently H or OA$^4$; A, A$^1$, A$^2$, A$^3$ and A$^4$ are each independently hydrogen, C$_{1-18}$ alkanoyl or

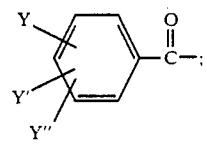

and Y, Y', Y" are each independently hydrogen, $C_{1-4}$ alkyl, $C_{1-4}$ alkoxy or halogen; or the pharmaceutically acceptable salts of the aforesaid compounds.

2. A compound according to claim 1 which has the formula

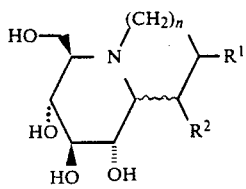

wherein n is 1 or 2; and $R^1$ and $R^2$ are independently H or $OA^4$; A, $A^1$, $A^2$, $A^3$ and $A^4$ are each independently hydrogen, $C_{1-18}$ alkanoyl or

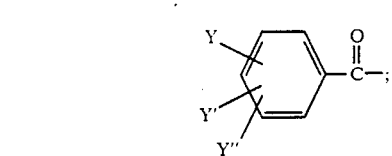

and Y, Y', Y" are each independently hydrogen, C6hd 1-4 alkyl, $C_{1-4}$ alkoxy or halogen; or the pharmaceutically acceptable salts of the aforesaid compounds.

3. A compound according to claim 1 which has the formula

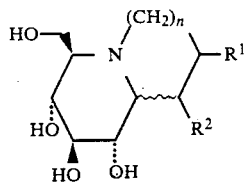

wherein n is 1 or 2; and $R^1$ and $R^2$ are independently H or OH.

4. A compound according to claim 1 which is [5R-(5α,6β,7α,8β,8aα)octahydro -6,7,8-trihydroxy-5-hydroxymethylindolizine.

5. A method for treating a retroviral infection in a patient which comprises administering to the patient an effective amount of a compound of the formula:

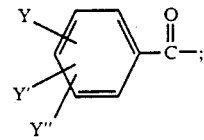

wherein n is 1 or 2; $R^1$ and $R^2$ are independently H or $OA^4$; A, $A^1$, $A^2$, $A^3$ and $A^4$ are each independently hydrogen, $C_{1-18}$ alkanoyl or

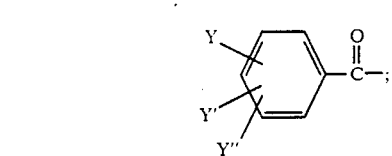

and Y, Y', Y" are each idependently hydrogen, $C_{1-4}$ alkyl, $C_{1-4}$ alkoxy or halogen; or the pharmaceutically acceptable salts of the aforesaid compounds.

6. A method according to claim 5 wherein the compound used is [5R(5α,6β,7α,8β,8aα)]octahydro-6,7,8-trihydroxy-5-hydroxymethylindolizine.

7. A method according to claim 5 wherein the compound used is [1S-(1α,2β,3α,4β,9α,9aβ)]-octahydro-4-hydroxymethyl) -2H-quinolizine-1,2,3,9-tetrol 9-benzoate.

8. A method according to claim 5 wherein the compound used is [1S-(1α,2β,3α,4β,9α,9aβ)]-octahydro-4-(hydroxymethyl) -2H-quinolizine-1,2,3,9-tetrol hydrochloride.

9. A method for treating diabetes and hyperglycemic conditions in mammals which comprises administrating an effective amount of a compound of the formula:

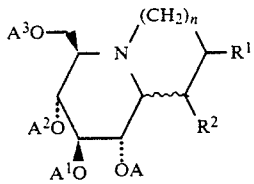

wherein n is 1 or 2; $R^1$ and $R^2$ are independently H or $OA^4$; A, $A^1$, $A^2$, $A^3$ and $A^4$ are each independently hydrogen, $C_{1-18}$ alkanoyl or

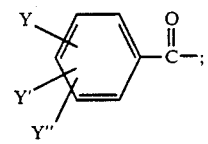

and Y, Y', Y" are each independently hydrogen, $C_{1-4}$ alkyl, $C_{1-4}$ alkoxy or halogen; or the pharmaceutically acceptable salts of the aforesaid compounds.

10. A method according to claim 9 wherein the compound is [5R-(5α,6β,7α, 8β,8aα)]octahydro-6,7,8-trihydroxy-5-hydroxymethylindolizine (VII).

* * * * *

UNITED STATES PATENT AND TRADEMARK OFFICE
CERTIFICATE OF CORRECTION

PATENT NO. : 5,028,614

DATED : July 2, 1991

INVENTOR(S) : Paul S. Liu, Mohinder S. Kang, Roland S. Roberts and Barry L. Rhinehart It is certified that error appears in the above-identified patent and that said Letters Patent is hereby corrected as shown below:

At Column 1, line 12, the patent reads "α,6β," and should read -- (1α,6β, --.

At Column 1, line 37, the patent reads "OA4" and should read -- $OA^4$ --.

At Column 1, line 38, the patent reads "C1-18" and should read -- $C_{1-18}$ --.

At Column 1, line 47, the patent reads "rr" and should read -- or --.

At Column 1, line 55, the patent reads "secon attached" and should read -- second atom attached --.

At Column 1, line 60, the patent reads "grOupS" and should read -- groups --.

At Column 2, line 7, the patent reads "inor9anic" and should read -- inorganic --.

At Column 4, line 60, the patent reads "compuond" and should read -- compound --.

At Column 6, line 21, the patent reads "2methoxy" and should read -- 2-methoxy --.

At Column 9, line 23, the patent reads "$(G_3M_s$" and should read -- $(G_3M_9$ --.

At Column 9, line 24, the patent reads "α-9lucosidase" and should read -- α-glucosidase --.

At Column 10, line 29, the patent reads "qlYcero-L-qulo" and should read -- glycero-L-gulo --.

At Column 10, line 29, the patent reads "(8.29" and should read -- (8.2g --.

At Column 10, line 44, the patent reads "(3.7 9, 5.4" and should read -- (3.7 g, 5.4 --.

At Column 10, line 46, the patent reads "(2.7 9," and should read -- (2.7 g, --.

At Column 12, line 18, the patent reads "hYdroxymethyl" and should read -- hydroxymethyl --.

UNITED STATES PATENT AND TRADEMARK OFFICE
CERTIFICATE OF CORRECTION

PATENT NO. : 5,028,614

DATED : July 2, 1991

INVENTOR(S) : Paul S. Liu, Mohinder S. Kang, Roland S. Roberts and Barry L.

It is certified that error appears in the above-identified patent and that said Letters Patent is hereby corrected as shown below:

Column 12, line 44, the patent reads "qlvcero" and should read -- glycero --.

Column 12, line 45, the patent reads "oulo" and should read -- gulo --.

Column 12, line 67, the patent reads "(2α,3" and should read -- (2α,3α --.

Column 13, line 4, the patent reads "PhCH2OH)" and should read -- PhCH$_2$OH) --.

Column 13, line 11, the patent reads "AlH3" and should read -- AlH$_3$ --.

Column 14, line 7, the patent reads "(m, 11H)" and should read -- (m, 1H) --.

Column 14, line 52, the patent reads "-6[(" and should read -- -6-[( --.

Column 15, line 6, the patent reads "1:1 as a clear colorless oil (0.34 g)" and should read -- 1:1 ethyl acetate:hexane) to yield crude N-debenzylated alcohol as a clear colorless oil (0.34g) --.

Column 15, line 44, the patent reads "hyqroscopic" and should read -- hygroscopic --.

Column 16, line 17, the patent reads "(CI13 CH$_4$)" and should read -- (CI-CH$_4$) --.

Column 16, line 42, the patent reads "cm-1" and should read -- cm$^{-1}$ --.

Column 16, line 43, the patent reads "(CI-CH4)" and should read -- (CI-CH$_4$) --.

Column 17, line 34, the patent reads "C6hd1-4 alkyl," and should read -- C$_{1-4}$ alkyl --.

Column 17, line 56, the patent reads "8aα)" and should read -- 8aα)] --.

Column 18, line 21, the patent reads "idependently" and should read -- independently --.

UNITED STATES PATENT AND TRADEMARK OFFICE
CERTIFICATE OF CORRECTION

PATENT NO. : 5,028,614

DATED : July 2, 1991

INVENTOR(S) : Paul S. Liu, Mohinder S. Kang, Roland S. Roberts and Barry L.

It is certified that error appears in the above-identified patent and that said Letters Patent is hereby corrected as shown below:

```
  Column 18, line 25, the patent reads "[5R(" and should read
-- [5R-( --.
  ABSTRACT, line 4 , "2,6-dideoxy-2,6-dideoxy-2,6-imino"
should read -- 2,6-dideoxy-2,6-imino --.
```

Signed and Sealed this

Twelfth Day of January, 1993

Attest:

DOUGLAS B. COMER

Attesting Officer

Acting Commissioner of Patents and Trademarks